United States Patent

Albaugh

[11] Patent Number: 5,510,480
[45] Date of Patent: Apr. 23, 1996

[54] CERTAIN AZACYCLOALKYL IMIDAZOPYRIMIDINES: A NEW CLASS OF GABA BRAIN RECEPTOR LIGANDS

[75] Inventor: Pamela Albaugh, Clinton, Conn.

[73] Assignee: Neurogen Corporation, Branford, Conn.

[21] Appl. No.: 273,497

[22] Filed: Jul. 11, 1994

Related U.S. Application Data

[63] Continuation of Ser. No. 971,765, filed PCT/US91/0454, Jun. 24, 1991, Pat. No. 5,328,912, which is a continuation-in-part of Ser. No. 557,577, Jun. 24, 1990, Pat. No. 5,095,015.

[51] Int. Cl.$^6$ .................. C07D 471/12; C07D 243/12; A61K 31/55; A61K 31/505
[52] U.S. Cl. ............ 544/251; 540/518; 540/521
[58] Field of Search .................. 544/251; 514/267, 514/214, 215; 540/578, 521

[56] References Cited

U.S. PATENT DOCUMENTS

| | | | |
|---|---|---|---|
| 4,643,999 | 2/1987 | Tully | 514/258 |
| 4,713,383 | 12/1987 | Francis et al. | 514/267 |
| 4,831,013 | 5/1989 | Francis | 514/23 |

FOREIGN PATENT DOCUMENTS

| | | |
|---|---|---|
| 181282 | 5/1986 | European Pat. Off. . |
| 217748 | 4/1987 | European Pat. Off. . |
| 263071 | 4/1988 | European Pat. Off. . |

*Primary Examiner*—Cecilia Tsang
*Attorney, Agent, or Firm*—Banner & Allegretti, Ltd.

[57] ABSTRACT

The invention encompasses compounds of the formula:

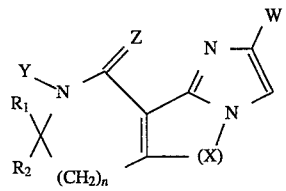

and the pharmaceutically acceptable non-toxic salts thereof wherein n is 0, 1, or 2, X is

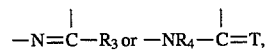

Z is $H_2$, oxygen or sulfur, and $R_1$, $R_2$, $R_3$, $R_4$, T, W, and Y are defined variables.

These compounds are highly selective agonists or inverse agonists for the GABAa brain receptors and are useful in the diagnosis and treatment of anxiety, sleep, and seizure disorders, overdose with benzodiazepine type drugs, and enhancement of alertness.

12 Claims, 2 Drawing Sheets

COMPOUND 1

COMPOUND 13

COMPOUND 14

COMPOUND 21

COMPOUND 22

COMPOUND 36

COMPOUND 44

COMPOUND 49

CERTAIN AZACYCLOALKYL IMIDAZOPYRIMIDINES: A NEW CLASS OF GABA BRAIN RECEPTOR LIGANDS

This is a continuation of application Ser. No. 07/971,765, filed filed PCT/US91/0454, Jun. 24, 1991 now U.S. Pat. No. 5,328,912 which is a continuation-in-part of application Ser. No. 07/557,577 filed Jun. 24, 1990 now U.S. Pat. No. 5,095,015.

BACKGROUND OF THE INVENTION

1. Field of the Invention

This invention relates to certain azacycloalkyl imidazopyrimidines which selectively bind to GABAa receptors. This invention also relates to pharmaceutical compositions comprising such compounds. It further relates to the use of such compounds in treating anxiety, sleep and seizure disorders, and overdoses of benzodiazepinetype drugs, and enhancing alertness. The interaction of those compounds with a GABA binding site, the benzodiazepine (BDZ) receptor, is described. This interaction results in the pharmacological activities of these compounds.

2. Description of the Related Art

γ-Aminobutyric acid (GABA) is regarded as one of the major inhibitory amino acid transmitters in the mammalian brain. Over 30 years have elapsed since its presence in the brain was demonstrated (Roberts & Frankel, J. Biol. Chem. 187: 55–63, 1950; Udenfriend, J. Biol. Chem. 187: 65–69, 1950). Since that time, an enormous amount of effort has been devoted to implicating GABA in the etiology of seizure disorders, sleep, anxiety and cognition (Tallman and Gallager, Ann. Rev. Neuroscience 8: 21–44, 1985). Widely, although unequally, distributed through the mammalian brain, GABA is said to be a transmitter at approximately 30% of the synapses in the brain. In most regions of the brain, GABA is associated with local inhibitory neurons and only in two regions is GABA associated with longer projections. GABA mediates many of its actions through a complex of proteins localized both on cell bodies and nerve endings; these are called GABAa receptors. Postsynaptic responses to GABA are mediated through alterations in chloride conductance that generally, although not invariably, lead to hyperpolarization of the cell. Recent investigations have indicated that the complex of proteins associated with postsynaptic GABA responses is a major site of action for a number of structurally unrelated compounds capable of modifying postsynaptic responses to GABA. Depending on the mode of interaction, these compounds are capable of producing a spectrum of activities (either sedative, anxiolytic, and anticonvulsant, or wakefulness, seizures, and anxiety).

1,4-Benzodiazepines continue to be among the most widely used drugs in the world. Principal among the benzodiazepines marketed are chlordiazepoxide, diazepam, flurazepam, and triazolam. These compounds are widely used as anxiolytics, sedative-hypnotics, muscle relaxants, and anticonvulsants. A number of these compounds are extremely potent drugs; such potency indicates a site of action with a high affinity and specificity for individual receptors. Early electrophysiological studies indicated that a major action of benzodiazepines was enhancement of GABAergic inhibition. The benzodiazepines were capable of enhancing presynaptic inhibition of a monosynaptic ventral root reflex, a GABA-mediated event (Schmidt et al., 1967, Arch. Exp. Path. Pharmakol. 258: 69–82). All subsequent electrophysiological studies (reviewed in Tallman et al. 1980, Science 207:274–81. Haefley et al., 1981, Handb. Exptl. Pharmcol. 33: 95–102) have generally confirmed this finding, and by the mid-1970s, there was a general consensus among electrophysiologists that the benzodiazepines could enhance the actions of GABA.

With the discovery of the "receptor" for the benzodiazepines and the subsequent definition of the nature of the interaction between GABA and the benzodiazepines, it appears that the behaviorally important interactions of the benzodiazepines with different neurotransmitter systems are due in a large part to the enhanced ability of GABA itself to modify these systems. Each modified-system, in turn, may be associated with the expression of a behavior.

Studies on the mechanistic nature of these interactions depended on the demonstration of a high-affinity benzodiazepine binding site (receptor). Such a receptor is present in the CNS of all vertebrates phylogenetically newer than the boney fishes (Squires & Braestrup 1977, Nature 166: 732–34, Mohler & Okada, 1977, Science 198: 854–51, Mohler & Okada, 1977, Br. J. Psychiatry 133: 261–68). By using tritiated diazepam, and a variety of other compounds, it has been demonstrated that these benzodiazepine binding sites fulfill many of the criteria of pharmacological receptors; binding to these sites in vitro is rapid, reversible, stereospecific, and saturable. More importantly, highly significant correlations have been shown between the ability of benzodiazepines to displace diazepam from its binding site and activity in a number of animal behavioral tests predictive of benzodiazepine potency (Braestrup & Squires 1978, Br. J. Psychiatry 133: 249–60, Mohler & Okada, 1977, Science 198: 854–51, Mohler & Okada, 1977, Br. J. Psychiatry 133: 261–68). The average therapeutic doses of these drugs in man also correlate with receptor potency (Tallman et al. 1980, Science 207: 274–281).

In 1978, it became clear that GABA and related analogs could interact at the low affinity (I μM) GABA binding site to enhance the binding of benzodiazepines to the clonazepan-sensitive site (Tallman et al. 1978, Nature, 274: 383–85). This enhancement was caused by an increase in the affinity of the benzodiazepine binding site due to occupancy of the GABA site. The data were interpreted to mean that both GABA and benzodiazepine sites were allosterically linked in the membrane as part of a complex of proteins. For a number of GABA analogs, the ability to enhance diazepam binding by 50% of maximum and the ability to inhibit the binding of GABA to brain membranes by 50% could be directly correlated. Enhancement of benzodiazepine binding by GABA agonists is blocked by the GABA receptor antagonist (+) bicuculline; the stereoisomer (−) bicuculline is much less active (Tallman et al., 1978. Nature, 274: 383–85).

Soon after the discovery of high affinity binding sites for the benzodiazepines, it was discovered that a triazolopyridazine could interact with benzodiazepine receptors in a number of regions of the brain in a manner consistent with receptor heterogeneity or negative cooperativity. In these studies, Hill coefficients significantly less than one were observed in a number of brain regions, including cortex, hippocampus, and striatum. In cerebellum, triazolopyridazine interacted with benzodiazepine sites with a Hill coefficient of 1 (Squires et al., 1979, Pharma. Biochem. Behav. 10: 825–30, Klepner et al. 1979, Pharmacol. Biochem. Behav. 11: 457–62). Thus, multiple benzodiazepine receptors were predicted in the cortex, hippocampus, striatum, but not in the cerebellum.

Based on these studies, extensive receptor autoradiographic localization studies were carried out at a light microscopic level. Although receptor heterogeneity has been demonstrated (Young & Kuhar 1980, J. Pharmacol. Exp. Ther. 212: 337–46, (Young et al., 1981 J. Pharmacol. Exp. Ther. 216: 425–430, Niehoff et al. 1982, 1. J. Pharmacol. Exp. Ther. 221: 670–75), no simple correlation between localization of receptor subtypes and the behaviors associated with the region has emerged from the early studies. In addition, in the cerebellum, where one receptor was predicted from binding studies, autoradiography revealed heterogeneity of receptors (Niehoff et al., 1982, J. Pharmacol. Exp. Ther. 221: 70–75).

A physical basis for the differences in drug specificity for the two apparent subtypes of benzodiazepine sites has been demonstrated by Sieghart & Karobath, 1980, Nature 286: 285-87. Using gel electrophoresis in the presence of sodium dodecyl sulfate, the presence of several molecular weight receptors for the benzodiazepines has been reported. The receptors were identified by the covalent incorporation of radioactive flunitrazepam, a benzodiazepine which can covalently label all receptor types. The major labeled bands have moelcular weights of 50,000 to 53,000, 55,000, and 57,000 and the triazolopyridazines inhibit labeling of the slightly higher molecular weight forms (53,000, 55,000, 57,000) (Seighart et al. 1983, Eur. J. Pharmacol. 88: 291–99).

At that time, the possibility was raised that the multiple forms of the receptor represent "isoreceptors" or multiple allelic forms of the receptor (Tallman & Gallager 1985, Ann. Rev. Neurosci. 8, 21–44). Although common for enzymes, genetically distinct forms of receptors have not generally been described. As we begin to study receptors, using specific radioactive probes and electrophoretic techniques, it is almost certain that isoreceptors will emerge as important in investigations of the etiology of psychiatric disorders in people.

The GABAa receptor subunits have been cloned from bovine and human cDNA libraries (Schoenfield et al., 1988; Duman et al., 1989). A number of distinct cDNAs were identified as subunits of the GABAa receptor complex by cloning and expression. These are categorized into ∝, β, γ, δ, ε, and provide a molecular basis for the GABAa receptor heterogeneity and distinctive regional pharmacology (Shivvers et al., 1980; Levitan et al., 1989). The γ subunit appears to enable drugs like benzodiazepines to modify the GABA responses (Pritchett et al., 1989). The presence of low Hill coefficients in the binding of ligands to the GABAa receptor indicates unique profiles of subtype specific pharmacological action.

Drugs that interact at the GABAa receptor can possess a spectrum of pharmacological activities depending on their abilities to modify the actions of GABA. For example, the beta-carbolines were first isolated based upon their ability to inhibit competitively the binding of diazepam to its binding site (Nielsen et al., 1979, Life Sci. 25: 679–86). The receptor binding assay is not totally predictive about the biological activity of such compounds; agonists, partial agonists, inverse agonists, and antagonists can inhibit binding. When the beta-carboline structure was determined, it was possible to synthesize a number of analogs and test these compounds behaviorally. It was immediately realized that the beta-carbolines could antagonize the actions of diazepam behaviorally (Tenen & Hirsch, 1980, Nature 288: 609–10). In addition to this antagonism, beta-carbolines possess intrinsic activity of their own opposite to that of the benzodiazepines; they become known as inverse agonists.

In addition, a number of other specific antagonists of the benzodiazepine receptor were developed based on their ability to inhibit the binding of benzodiazepines. The best studied of these compounds is an imidazodiazepine, (Hunkeler et al., 1981, Nature 290: 514–516). This compound is a high affinity competitive inhibitor of benzodiazepine and beta-carboline binding and is capable of blocking the pharmacological actions of both these classes of compounds. By itself, it possesses little intrinsic pharmacological activity in animals and humans (Hunkeler et al., 1981, Nature 290: 514–16; Darragh et al., 1983, Eur. J. Clin. Pharmacol. 14: 569–70). When a radiolabeled form of this compound was studied (Mohler & Richards, 1981, Nature 294: 763–65), it was demonstrated that this compound would interact with the same number of sites as the benzodiazepines and beta-carbolines, and that the interactions of these compounds were purely competitive. This compound is the ligand of choice for binding to GABAa receptors because it does not possess receptor subtype specificity and measures each state of the receptor.

The study of the interactions of a wide variety of compounds similar to the above has led to the categorizing of these compounds. Presently, those compounds possessing activity similar to the benzodiazepines are called agonists. Compounds possessing activity opposite to benzodiazepines are called inverse agonists, and the compounds blocking both types of activity have been termed antagonists. This categorization has been developed to emphasize the fact that a wide variety of compounds can produce a spectrum of pharmacological effects, to indicate that compounds can interact at the same receptor to produce opposite effects, and to indicate that beta-carbolines and antagonists with intrinsic anxiogenic effects are not synonymous.

A biochemical test for the pharmacological and behavioral properties of compounds that interact with the benzodiazepine receptor continues to emphasize the interaction with the GABAergic system. In contrast to the benzodiazepines, which show an increase in their affinity due to GABA (Tallman et al., 1978, Nature 274: 383–85, Tallman et al., 1980, Science 207: 274–81), compounds with antagonist properties show little GABA shift (i.e., change in receptor affinity due to GABA) (Mohler & Richards 1981, Nature 294: 763–65), and the inverse agonists actually show a decrease in affinity due to GABA [(Braestrup & Nielson 1981, Nature 294: 472–474)]. Thus, the GABA shift predicts generally the expected behavioral properties of the compounds.

Various compounds have been prepared as benzodiazepine agonists and antagonists. For example, U.S. Pat. Nos. 4,713,383, and 4,643,999 and Eur. Patent Applications Nos. 181,282, 219,748 and 263,071 teach various benzodiazpine agonists and antagonists useful in the treatment of anxiety.

U.S. Pat. No. 4,643,999 discloses compounds of the formula:

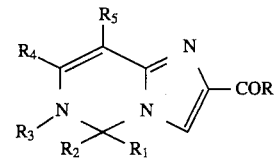

wherein R is an aryl of 6 to 12 carbon atoms, $R_1$ is selected from the group consisting of hydrogen and alkyl, alkoxy and alkylthio of 1 to 5 carbon atoms when $R_2$ and $R_3$ together form a carbon-nitrogen bond or $R_1$ and $R_2$ together are =O when $R_3$ is selected from the group consisting of hydrogen, alkyl of 1 to 5 carbon atoms and alkenyl of 2 to 5 carbon atoms, $R_4$ is selected from the group consisting of alkoxy and alkylthio of 1 to 5 carbon atoms, $R_5$ is selected from the group consisting of hydrogen and alkyl of 1 to 5 carbon atoms, and their non-toxic, pharmaceutically acceptable acid addition salts.

U.S. Pat. No. 4,713,383 teaches compounds of the formula:

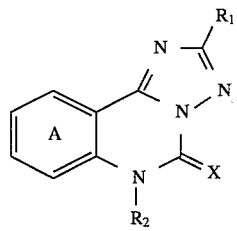

wherein $R_1$=(un)substituted Ph, (dihydro)furanyl, tetrahydrofuranyl, (dihydro)thienyl, tetrahydrothienyl, pyranyl, ribofuranosyl, all C-attached;

$R_2$=H, alkyl; X=O, S, $R_3$N; $R_3$=H, alkenyl, alkynyl, $C_{3-20}$ cycloalkyl, (un)substituted alkyl, aryl, aralkyl, where aryl is Ph, pyridinyl, thienyl, furanyl; ring A may be substituted by alkyl, alkoxy, halo, amino, alkylthio, etc.

European Patent Application EP 181,282 discloses compounds of the formula:

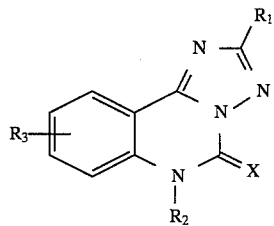

wherein $R_1$=(substituted) Ph or heterocycle;

$R_2$= H, alkyl, alkenyl, hydroxyalkyl, aralkyl, aralkenyl, aryl;

$R_3$= H, alkyl, alkoxy, HO, halo, $F_3C$, $O_3N$, $H_2N$, alkylthio, alkylsulfinyl, alkyisulfonyl, aralkoxy; X=O, S, $NR_4$;

$R_4$= H, alkyl, aralkyl, cycloalkyl, alkenyl, alkynyl, aryl, (substituted) aminoaklyl, hydroxyalkyl. European Patent Application EP 217,748 teaches compounds of the formula:

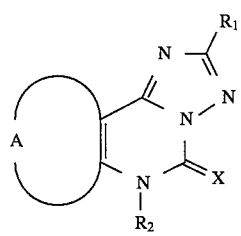

wherein

A=atoms to complete a fused, (un)substituted, (un)saturated, carbocyclic or heterocyclic ring comprising C, O, N, and S;

X=O, S, RN;

R= H, OH, hydroxyalkyl, aryl, $H_2NC(:NH)$, alkyl, alkenyl, alkynyl, optionally with hetero atom interrupters;

R=(un)substituted carbocyclyl, heterocyclyl;

$R_2$= (un)substituted Ph.

European Patent Application EP 263,071 discloses compounds of the formula

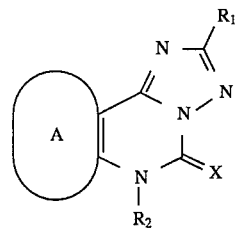

wherein

X=O, NR, S:

R=H, lower alkyl, alkenyl, alkynyl;

$R_1$= (substituted) Ph, furyl, thienyl, pyridyl, pyrrolyl, etc;

ring A=$C_{5-8}$ cycloalkene, heterocycle, etc., each ring A being unsubstituted or substituted by lower alkyl, alkoxy, OH, halogen, $CF_3$, $NO_2$, carbamoyl, carbamoylalkyl, etc.

These compounds differ from the compounds of the present invention. U.S. Pat. No. 4,713,383, and European Patent Applications Nos. 181,282, 217,748 and 263,071 each teach carbocyclic compounds having an additional nitrogen atom in the carbocyclic system. U.S. Pat. No. 4,643,999 teaches imidazopyrimidines lacking the aryl substituents at position 2, the nitrogen in the ring system at position 9, and other various ring substituents of the compounds of the present invention.

SUMMARY OF THE INVENTION

This invention provides novel compounds of the general Formula I which interact with a modulatory site on one or more subtypes of the brain GABAa receptor and possess intrinsic activites ranging from agonist to inverse agonist.

The invention provides pharmaceutical compositions comprising compounds of Formula I. The invention also provides compounds useful in enhancing alertness, treatment of seizure, anxiety, and sleep disorders, and treatment of benzodiazepine overdoses. Accordingly, a broad embodiment of the invention is directed to compounds of Formula I.

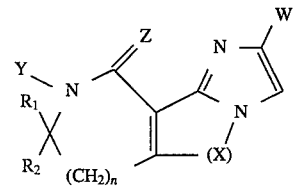

and the pharmaceutically acceptable non-toxic salts thereof wherein

Z is $H_2$, oxygen or sulfur;

$R_1$ and $R_2$ hydrogen or straight chain or branched lower alkyl having 1–6 carbon atoms;

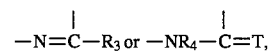

X is
with the proviso that when

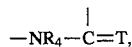

T is oxygen or sulfur, and when X is

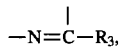

is hydrogen, halogen, aryloxy, alkoxy having 1–6 carbon atoms or $OCOR_5$ where $R_5$ is hydrogen, straight or branched chain alkyl having 1–6 carbon atoms, alkoxy having 1–6 carbon atoms, or dialkylamino where each alkyl has 1–6 carbon atoms, and $R_4$ is H, lower alkyl having 1–6 carbon atoms or $COR_6$ where $R_6$ is hydrogen, straight or branched chain alkyl having 1–6 carbon atoms, alkoxy having 1–6 carbon atoms or dialkylamino where each alkyl has 1–6 carbon atoms;

W is phenyl, 2- or 3-thienyl or 2-, 3-, or 4-pyridyl;

or phenyl, 2- or 3-thienyl or 2-, 3-, or 4-pyridyl, each of which is mono or disubstituted with halogen, lower alkyl, or straight or branched chain lower alkoxy having 1–6 carbon atoms;

Y is i) hydrogen, phenyl, 2- or 3-thienyl, 2-, 3- or 4-pyridyl, 2- or 4(5)-imidazolyl, 2-pyrimidinyl, or 1-indanyl;

ii) phenyl, 2- or 3-thienyl, 2-, 3- or 4-pyridyl, 2- or 4(5)-imidazolyl, or 2-pyrimidinyl, each of which is mono or disubstituted with halogen, lower alkyl having 1–6 carbon atoms, lower alkoxy having 1–6 carbon atoms, or alkoxylalkyl where the alkoxy portion is straight or branched chain alkoxy having 1–6 carbon, atoms and the alkyl portion is straight or branched chain alkyl having 1–6 carbon atoms;

iii) straight or branched chain alkyl having 1–6 carbon atoms;

iv) straight or branched chain alkyl having 1–6 carbon atoms, wherein each alkyl is substituted with the groups of ii:

v) cycloalkyl having 3–10 carbon atoms, cycloalkyl alkyl where the cycloalkyl portion has 3–7 carbon atoms and the alkyl portion has 1–6 carbon atoms;

vi) aminoalkyl where the alkyl portion is straight or branched chain alkyl having 1–6 carbon atoms, or mono or dialkyl aminoalkyl where each alkyl is a straight or branched chain alkyl having 1–6 carbon atoms; or vii) $COR_7$ or $SO_2R_7$ where $R_7$ is straight or branched chain lower alkyl having 1–6 carbon atoms, phenyl, 2- or 3-thienyl, 2-, 3- or 4-pyridyl, 2- or 4(5)-imidazolyl, or 2-pyrimidinyl; or $R_7$ is phenyl, 2- or 3-thienyl, 2-, 3- or 4-pyridyl, 2 or 4(5)-imidazolyl, or 2-pyrimidinyl each of which may be mono or disubstituted with halogen, lower alkyl having 1–6 carbon atoms, straight or branched alkoxy having 1–6 carbon atoms, or alkoxyalkyl where the alkoxy portion is straight or branched chain alkoxy having 1–6 carbon atoms and the alkyl portion is straight or branched chain alkyl having 1–6 carbon atoms; and n is 0, 1, or 2.

These compounds, or prodrugs thereof, are highly selective agonists, antagonists, or inverse agonists at a modulatory site on one or more subtypes of the brain GABAa receptor and are useful in the diagnosis and treatment of anxiety, sleep, and seizure disorders, overdose with benzodiazepine drugs, and enhancement of memory.

DETAILED DESCRIPTION OF THE INVENTION

Figure 1A:
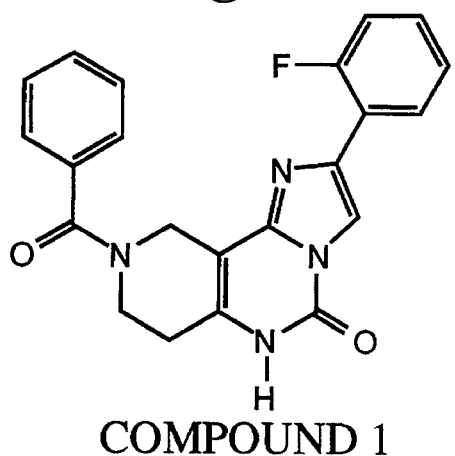
FIG. 1A–H shows representative examples of the present invention.
Figure 1B:
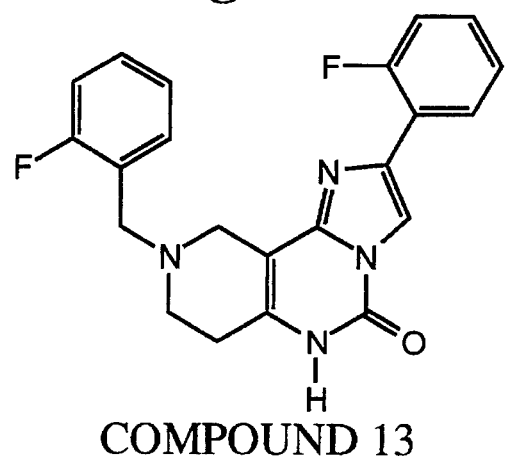
Figure 1C:
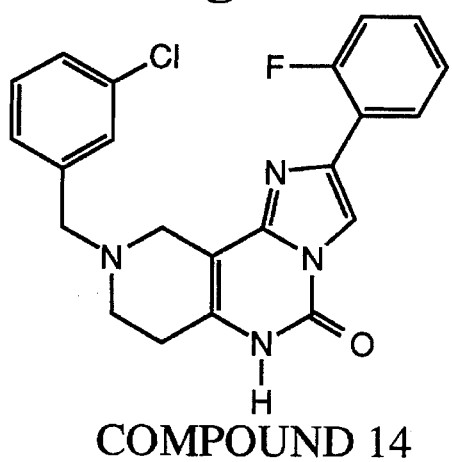
Figure 1D:
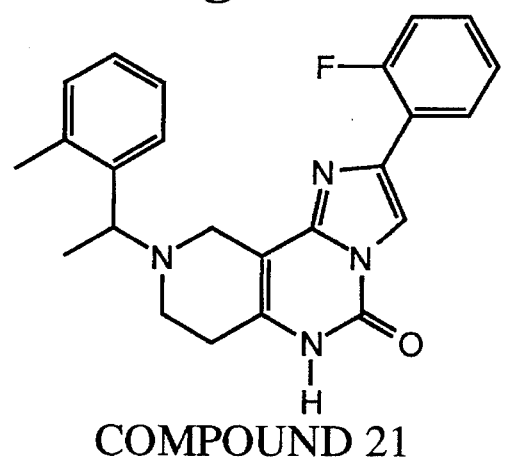
Figure 1E:
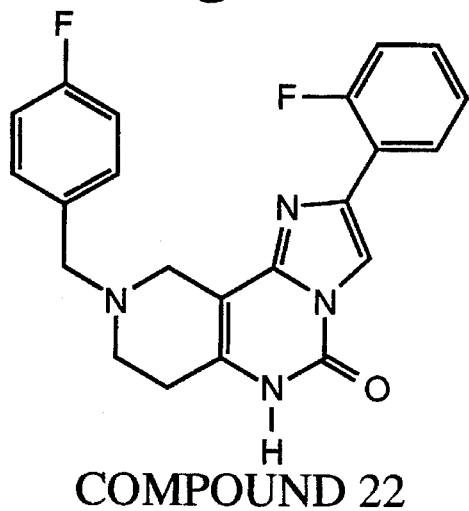
Figure 1F:
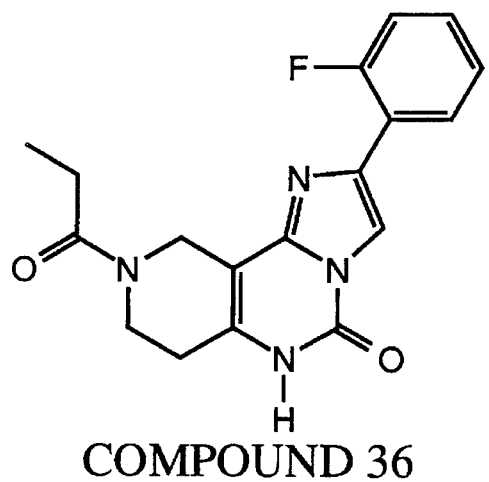
Figure 1G:
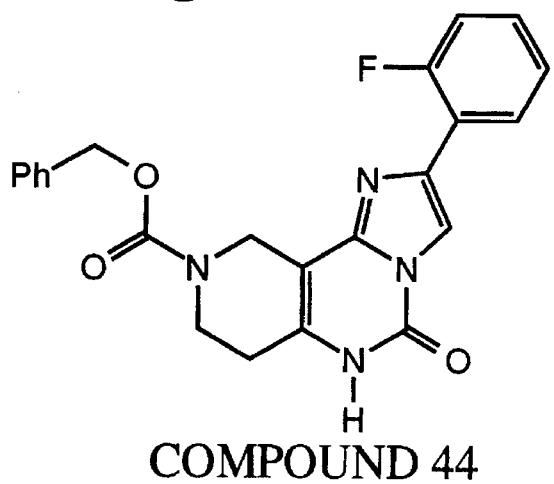
Figure 1H:
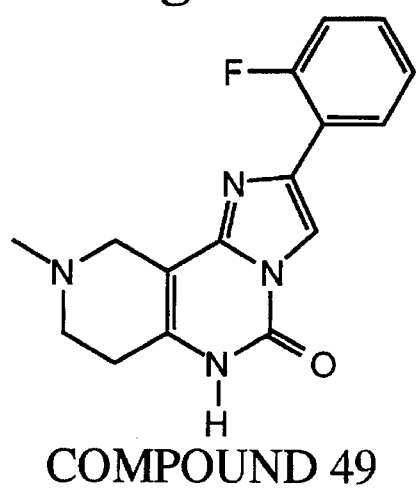

The novel compounds encompassed by the instant invention can be described by the following general formula I:

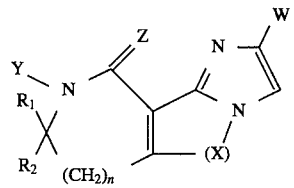

and the pharmaceutically acceptable non-toxic salts thereof wherein

Z is $H_2$, oxygen or sulfur;, $R_1$ and $R_2$ are hydrogen or straight chain or branched lower alkyl having 1–6 carbon atoms;

X is

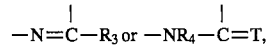

with the proviso that when X is

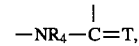

T is oxygen or sulfur, and when X is

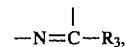

$R_3$ is hydrogen, halogen, aryloxy, alkoxy having 1–6 carbon atoms or $OCOR_5$ where $R_5$ is hydrogen, straight or branched chain alkyl having 1–6 carbon atoms, alkoxy having 1–6 carbon atoms, or dialkylamino where each alkyl has 1–6 carbon atoms, and $R_4$ is H, lower alkyl having 1–6 carbon atoms or $COR_6$ where $R_6$ is hydrogen, straight or branched chain alkyl having 1–6 carbon atoms, alkoxy having 1–6 carbon atoms or dialkylamino when each alkyl has 1–6 carbon atoms;

W is phenyl, 2- or 3-thienyl or 2-, 3-, or 4-pyridyl; or phenyl, 2- or 3-thienyl or 2-, 3-, or 4-pyridyl, each of which is mono or disubstituted with halogen, lower alkyl, or straight or branched chain lower alkoxy having 1–6 carbon atoms;

Y is i) hydrogen, phenyl, 2- or 3-thienyl, 2-, 3- or 4-pyridyl, 2- or 4(5)-imidazolyl, 2-pyrimidinyl, or 1-indanyl;

ii) phenyl, 2- or 3-thienyl, 2-, 3- or 4-pyridyl, 2- or 4(5)-imidazolyl, or 2-pyrimidinyl, each of which is mono or disubstituted with halogen, lower alkyl having 1–6 carbon atoms, lower alkoxy having 1–6 carbon atoms, or alkoxylalkyl where the alkoxy portion is straight or branched chain alkoxy having 1–6 carbon atoms and the alkyl portion is straight or branched chain alkyl having 1-6 carbon atoms;

iii) straight or branched chain alkyl having 1-6 carbon atoms;

iv) straight or branched chain alkyl having 1-6 carbon atoms, wherein each alkyl is substituted with the groups of ii;

v) cycloalkyl having 3-10 carbon atoms, cycloalkyl alkyl where the cycloalkyl portion has 3-7 carbon atoms and the alkyl portion has 1-6 carbon atoms;

vi) aminoalkyl where the alkyl portion is straight or branched chain alkyl having 1-6 carbon atoms, or mono, or dialkyl aminoalkyl where each alkyl is a straight or branched chain alkyl having 1-6 carbon atoms; or vii) $COR_7$ or $SO_2R_7$ where $R_7$ is straight or branched chain lower alkyl having 1–6 carbon atoms, phenyl, 2- or 3-thienyl, 2-, 3- or 4-pyridyl, 2- or 4(5)-imidazolyl, or 2-pyrimidinyl; or $R_7$ is phenyl, 2- or 3-thienyl, 2-, 3- or 4-pyridyl, 2- or 4(5)-imidazolyl, or 2-pyrimidinyl each of which may be mono or disubstituted with halogen, lower alkyl having 1-6 carbon atoms, straight or branched alkoxy having 1-6 carbon atoms, or alkoxyalkyl where the alkoxy portion is straight or branched chain alkoxy having 1-6 carbon atoms and the alkyl portion is straight or branched chain alkyl having 1-6 carbon atoms; and n is 0, 1, or 2.

The invention also encompasses compounds of formula II:

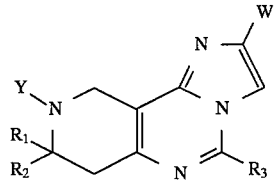

and the pharmaceutically acceptable non-toxic salts thereof wherein $R_1$ and $R_2$ are hydrogen or straight chain lower alkyl having 1-6 carbon atoms;

$R_3$ is hydrogen, halogen, aryloxy, alkoxy having 1–6 carbon atoms, or $OCOR_5$ where $R_5$ is hydrogen, straight or branched chain alkyl having 1-6 carbon atoms, alkoxy having 1-6 carbon atoms, or dialkylamino where each alkyl has 1-6 carbon atoms;

W is phenyl or phenyl monosubstituted with chlorine or 0 fluorine; and

Y is hydrogen, lower alkyl having 1–6 carbon atoms, alkanoyl having 1-6 carbon atoms, carboalkoxy having 1–6 alkyl carbon atoms, carbobenzyloxy, and pyridyl alkyl wherein the alkyl portion has 1-6 carbon atoms; or phenylalkyl or thienylalkyl, where the phenyl or thienyl portion is substituted with one or two chlorine or bromine atoms and the alkyl portion has 1-3 alkyl carbon atoms, The invention also encompassses compounds of formula III:

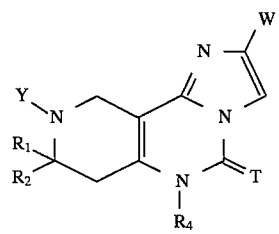

and the pharmaceutically acceptable non-toxic salts thereof wherein

T is oxygen or sulfur;

$R_1$ and $R_2$ are hydrogen or straight chain lower alkyl having 1–6 carbon atoms;

$R_4$ is hydrogen, lower alkyl, or $COR_5$ where $R_5$ is hydrogen, straight or branched chain alkyl having 1–6 carbon atoms, alkoxy having 1–6 carbon atoms, or dialkylamino where each alkyl has 1–6 carbon atoms;

W is phenyl or phenyl monosubstituted with chlorine or fluorine; and

Y is hydrogen, lower alkyl having 1–6 carbon atoms, alkanoyl having 1-6 carbon atoms, carboalkoxy having 1–6 alkyl carbon atoms, carbobenzyloxy, and pyridyl alkyl wherein the alkyl portion has 1-6 carbon atoms; or phenylalkyl or thienylalkyl, where the phenyl or thienyl portion is substituted with one or two chlorine or bromine atoms and the alkyl portion has 1–3 alkyl carbon atoms.

The invention also encompassses compounds of formula IV:

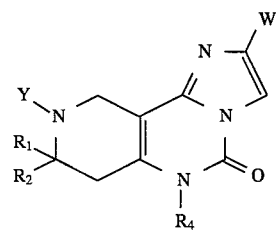

and the pharmaceutically acceptable non-toxic salts thereof wherein $R_1$ and $R_2$ are hydrogen or straight chain lower alkyl having 1–6 carbon atoms;

$R_4$ is hydrogen, lower alkyl or $COR_5$ where $R_5$ is hydrogen, straight or branched chain alkyl having 1–6 carbon atoms, alkoxy having 1–6 carbon atoms or dialkylamino where each alkyl has 1–6 carbon atoms;

W is phenyl or phenyl monosubstituted with chlorine or fluorine; and

Y is hydrogen, lower alkyl having 1–6 carbon atoms, alkanoyl having 1-6 carbon atoms, carboalkoxy having 1–6 alkyl carbon atoms, carbobenzyloxy, and pyridyl alkyl wherein the alkyl portion has 1-6 carbon atoms; or phenylalkyl or thienylalkyl, where the phenyl or thienyl portion is substituted with one or two chlorine or bromine atoms and the alkyl portion has 1–3 alkyl carbon atoms.

These compounds are highly selective agonists, antagonists, or inverse agonists at a modulatory site on one or more subtypes of the brain GABAa receptor, or prodrugs thereof, and are useful in the diagnosis and treatment of anxiety, sleep, and seizure disorders, overdose with benzodiazepine drugs, and enhancement of memory.

Non-toxic pharmaceutical salts include salts of acids such as hydrochloric, phosphoric, hydrobromic, sulfuric, sulfinic, formic, toluene sulfonic, hydroiodic, acetic and the like. Those skilled in the art will recognize a wide variety of non-toxic pharmaceutically acceptable addition salts.

Representative compounds of the present invention, which are encompassed by Formula I, include, but are not limited to the compounds in FIG. I and their pharmaceutically acceptable salts.

The pharmaceutical utility of compounds of this invention are indicated by the following assay for GABAa receptor activity.

Assays are carried out as described in Thomas and Tallman (J. Bio. Chem. 156: 9838–9842, J. Neurosci. 3:433–440, 1983). Rat cortical tissue is dissected and homogenized in 25 volumes (w/v) of 0.05 M Tris HCl buffer (pH 7.4 at 4° C.). The tissue homogenate is centrifuged in the cold (4°) at 20,000×g for 20'. The supernatant is decanted and the pellet is rehomogenized in the same volume of buffer and again centrifuged at 20,000×g. The supernatant is decanted and the pellet is frozen at −20° C. overnight. The pellet is then thawed and rehomogenized in 25 volume (original wt/vol) of buffer and the procedure is carried out twice. The pellet is finally resuspended in 50 volumes (w/vol of 0.05 M Tris HCl buffer (pH 7.4 at 40° C).

Incubations contain 100 µl of tissue homogenate, 100 µl of radioligand 0.5 nM ($^3$H-RO15-1788 specific activity 80 Ci/mmol), drug or blocker and buffer to a total volume of 500 µl. Incubations are carried for 30 min at 4° C. then are rapidly filtered through GFB filters to separate free and bound ligand. Filters arc washed twice with fresh 0.05 M Tris HCl buffer (pH 7.4 at 4° C.) and counted in a liquid scintillation counter. 1.0 µM diazepam is added to some tubes to determine nonspecific binding. Data are collected in triplicate determinations, averaged and % inhibition of total specific binding is calculated. Total Specific Binding=Total − Nonspecific. In some cases, the amounts of unlabeled drugs is varied and total displacement curves of binding are carried out. Data are converted to a form for the calculation of $IC_{50}$ and Hill Coefficient (nH).

Data for representative compounds of this invention are listed in Table I.

TABLE 1

| Compound Number[1] | $IC_{50}$ (µM) |
| --- | --- |
| 1 | 0.500 |
| 13 | 0.0024 |
| 14 | 0.100 |
| 21 | 0.0048 |
| 22 | 0.0038 |
| 36 | 0.010 |
| 44 | 0.010 |
| 49 | 0.030 |

[1]Compound numbers relate to compounds shown in FIG. I.

Compounds 13, 21 and 22 are particularly preferred embodiments of the present invention because of their potency in binding to the GABAa receptor.

The compounds of general formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, then is provided a pharmaceutical formulation comprising a compound of general formula I and a pharmaceutically acceptable carrier. One or more compounds of general formula I may be present in association with one or more non-toxic pharmaceutically acceptable carriers and/or diluents and/or adjuvants and if desired other active ingredients. The pharmaceutical compositions containing compounds of general formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented u hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive, oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth. naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitor or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of general formula I may also be administered in the form of suppositories for rectal administration of the drug. These compositions can be prepared by mixing the drug with a suitable nonirritating excipient which is solid at ordinary temperatures but liquid at the rectal temperature and will therefore melt in the rectum to release the drug. Such materials are cocoa butter and polyethylene glycols.

Compounds of general formula I may be administered parenterally in a sterile medium. The drug, depending on the vehicle and concentration used, can either be suspended or dissolved in the. vehicle. Advantageously, adjuvants such as local anaesthetics, preservatives and buffering agents can be dissolved in the vehicle.

Dosage levels of the order of from about 0.1 mg to about 140mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Compounds of the present invention are prepared according to Schemes I or II:

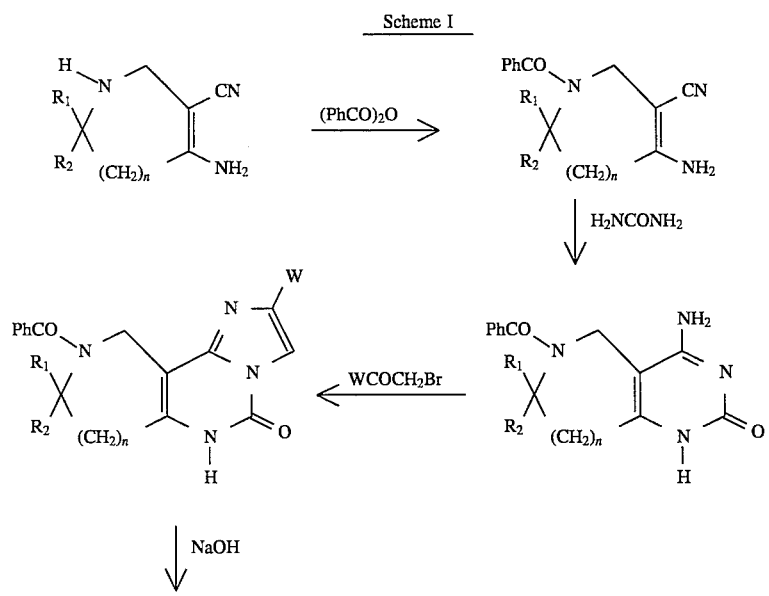

Scheme I

-continued
Scheme I

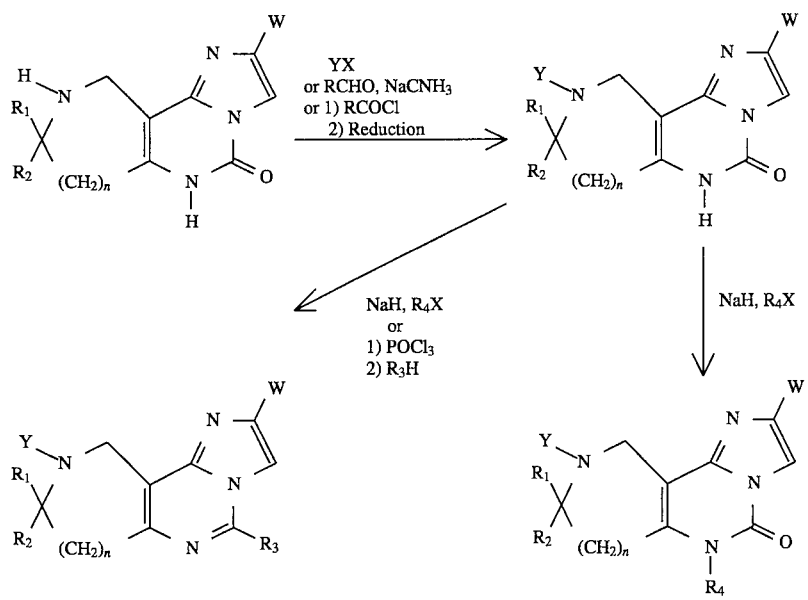

Scheme II

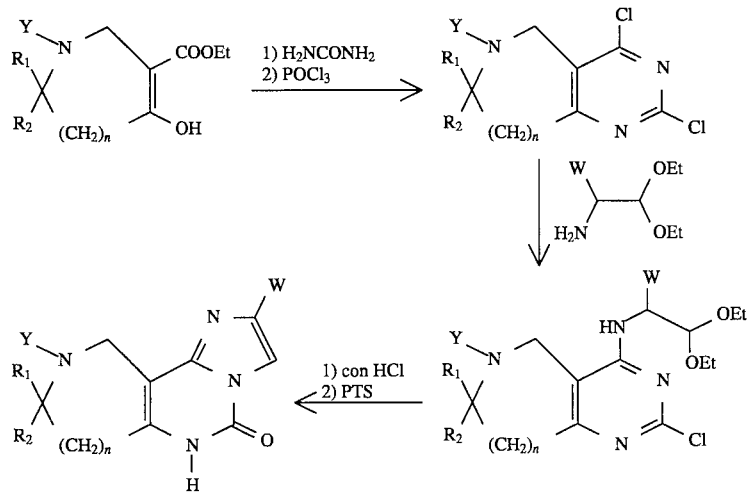

Where:

R$_1$ and R$_2$ are hydrogen or straight chain or branched lower alkyl having 1–6 carbon atoms;

R$_3$ is hydrogen, halogen, aryloxy, alkoxy having 1–6 carbon atoms or OCOR$_5$ where R$_5$ is hydrogen, straight or branched chain alkyl having 1–6 carbon atoms, alkoxy having 1–6 carbon atoms or dialkylamino where each alkyl has 1–6 carbon atoms;

R$_4$ is lower alkyl or COR$_5$ where R$_5$ is hydrogen, straight or branched chain alkyl having 1–6 carbon atoms, aryl, alkoxy having 1–6 carbon atoms or dialkylamino having 1–6 carbon atoms;

W is phenyl, 2- or 3-thienyl or 2-, 3-, or 4-pyridyl;

or phenyl, 2- or 3-thienyl or 2-, 3-, or 4-pyridyl, each of which is mono or disubstituted with halogen, lower alkyl, or straight or branched chain lower alkoxy having 1–6 carbon atoms;

Y is i) hydrogen, phenyl, 2- or 3-thienyl, 2-, 3- or 4-pyridyl, 2- or 4(5)-imidazolyl, 2-pyrimidinyl, or 1-indanyl;

ii) phenyl, 2- or 3-thienyl, 2-, 3- or 4-pyridyl, 2- or 4(5)-imidazolyl, or 2-pyrimidinyl, each of which is mono or disubstituted with halogen, lower alkyl having 1–6 carbon atoms, lower alkoxy having 1–6 carbon atoms, or alkoxylalkyl where the alkoxy portion is straight or branched chain alkoxy having 1–6 carbon atoms and the alkyl portion is straight or branched chain alkyl having 1–6 carbon atoms:

iii) straight or branched chain alkyl having 1–6 carbon atoms;

iv) straight or branched chain alkyl having 1–6 carbon atoms, wherein each alkyl is substituted with the groups of ii;

v) cycloalkyl having 3–10 carbon atoms, cycloalkyl alkyl where the cycloalkyl portion has 3—7 carbon atoms and the alkyl portion has 1–6 carbon atoms;

vi) aminoalkyl where the alkyl portion is straight or branched chain alkyl having 1–6 carbon atoms, or mono or dialkyl aminoalkyl where each alkyl is a straight or branched chain alkyl having 1–6 carbon atoms: or vii) $COR_7$ or $SO_2R_7$ where $R_7$ is straight or branched chain lower alkyl having 1–6 carbon atoms, phenyl, 2- or 3-thienyl, 2-, 3- or 4-pyridyl, 2- or 4(5)-imidazolyl, or 2-pyrimidinyl; or $R_7$ is phenyl, 2- or 3-thienyl, 2-, 3- or 4-pyridyl, 2- or 4(5)-imidazolyl, or 2-pyrimidinyl each of which may be mono or disubstituted with halogen, lower alkyl having 1–6 carbon atoms, straight or branched alkoxy having 1–6 carbon atoms, or alkoxyalkyl where the alkoxy portion is straight or branched chain alkoxy having 1–6 carbon atoms and the alkyl portion is straight or branched chain alkyl having 1–6 carbon atoms; and n is 0, 1, or 2.

Those having skill in the art will recognize that the starting materials may be varied and additional steps employed to produce compounds encompassed by the present invention, as demonstrated by the following examples.

The invention is illustrated further by the following examples which are not to be construed as limiting the invention in scope or spirit to the specific procedures described in them.

EXAMPLE I

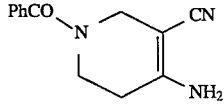

To a stirred suspension of 4-Amino-3-cyano-1,2,5,6-tetrahydropyridine (prepared according to a the procedure described by Taub et al., 1967, J. Chem. Soc. C: 1558) (95.51 g, 775 mmol) in pyridine (500 mL), benzoic anhydride (274 g, 1.20 mol) was added in portions over 1–2 hours. After stirring an additional 30 minutes, the precipitate was collected, washed first with toluene, then ether, and subsequently allowed to dry to afford 1-benzoyl-4-amino-3-cyano-1,2,5,6-tetrahydropyridine as a white solid, m.p. 178°–181° C.

EXAMPLE II

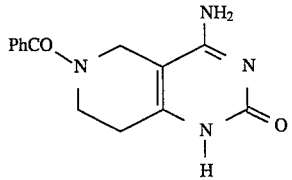

A slurry of 1-benzoyl-4-amino-3-cyano-1,2,5,6-tetrahydropyridine (35.23 g, 155 mmol) and urea (46.55 g, 775 mmol) in 2-(2-ethoxyethoxy)ethanol (75 mL) was gradually heated to about 205° C., and maintained at 205° C. for 90 minutes. Heating was ceased and hot water was *carefully* added while shaking the mixture. The mixture was vacuum filtered to collect the precipitate while hot. The precipitate was washed with hot water until the filtrate was colorless. The precipitate was then washed with ethanol until the flitrate was colorless, and then finally with ethyl acetate and allowed to dry to yield 6-benzoyl-4-amino- 6,7,8,9-tetrahydro-pyrido[3,4-e]pyrimidin-2-one as a light yellow solid.

EXAMPLE III

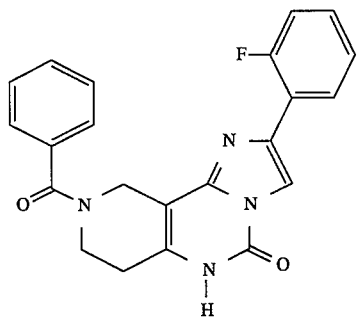

A mixture of 6-benzoyl-4-amino-6,7,8,9-tetrahydro-pyrido[3,4-e] pyrimidin-2-one (1 g, 3.7 mmol) and 1-bromo-2'-fluoroacetophenone (0.74 g, 3.7 mmol) in 8 mL of dimethylformamide (DMF) was heated at about 150° C. for 45 minutes. The reaction mixture was poured into ice water. and the precipitate collected to give 9-Benzoyl-2-(2-fluorophenyl)- 7,8,9,10-tetrahydro-imidazo[1,2-c]pyrido[3,4-e] pyrimidin-5(6H)-one (Compound 1). Later, a second crop of precipitate was collected as a cream-colored solid, m.p. 269°–271° C. (d).

EXAMPLE IV

The following compounds were prepared according to the procedures described in Examples I–III:

(a)  9-Benzoyl-2-(3-chlorophenyl)-7,8,9,10-tetrahydroimidazo[ 1,2-c]pyrido[3,4-e] pyrimidin-5(6H)-one(Compound 2), m.p. 250°– 253° C. (d).

(b)  9-Benzoyl-2-(3-fluorophenyl)-7,8,9,10-tetrahydroimidazo[ 1,2-c]pyrido[3,4-e] pyrimidin-5(6H)-one (Compound 3).

(c) 9-Benzoyl-2-phenyl-7,8,9,10-tetrahydro-imidazo[1,2-c] pyrido[3,4-e] pyrimidin-5(6H)-one(Compound 4).

(d)  9-Benzoyl-2-(4-fluorophenyl)-7,8,9,10-tetrahydroimidazo[ 1,2-c]pyrido[3,4-e] pyrimidin-5(6H)-one (Compound 5), m.p. 295°–300° C.

(e)  9-Benzoyl-2-(4-methoxyphenyl)-7,8,9,10-tetrahydroimidazo[ 1,2-c]pyrido[3,4-e] pyrimidin-5(6H)-one (Compound 6).

EXAMPLE V

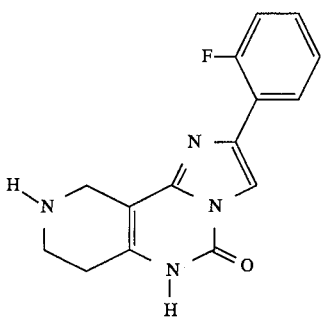

To a solution of 9-Benzoyl-2-(2-fluorophenyl)-7,8,9,10-tetrahydro-imidazo[ 1,2-c]pyrido[3,4-e] pyrimidin-5(6H)-one (435 mg, 1.1 mmol) in ethanol (5 mL) was added 5 mL of 50% aqueous sodium hydroxide. The mixture was refluxed for about 1 hour, and then poured into saturated aqueous ammonium chloride and extracted twice with 10% methanol/ethyl acetate. The combined organic layers were dried over magnesium sulfate, filtered, concentrated, and triturated with methanol/ether to give 2-(2-fluorophenyl)-7, 8,9,10-tetrahydroimidazo[ 1,2-c]pyrido[3,4-e] pyrimidin-5(6H)-one(Compound 7), m.p.> 310° C.

EXAMPLE VI

The following compounds were prepared according to the procedure described in Example V:

(a) 2-(2-Chlorophenyl)-7,8,9,10-tetrahydro-imidazo[1,2-c] pyrido[3,4-e] pyrimidin-5(6H)-one (Compund 8), m.p. 320°–322° C.

(b) 2-(3-Fluorophenyl)-7,8,9,10-tetrahydro-imidazo[1,2-c] pyrido[3,4-e] pyrimidin-5(6H)-one (Compound 9).

(c) 2-Phenyl-7,8,9,10-tetrahydro-imidazo[ 1,2-c]pyrido [3,4-e] pyrimidin-5(6H)-one (Compound 10), m.p. >310° C.

(d) 2-(4-Fluorophenyl)-7,8,9,10-tetrahydro-imidazo[1,2-c] pyrido[3,4-e] pyrimidin-5(6H)-one (Compound 11).

(e) 2-(4-Methoxyphenyl)-7,8,9,10-tetrahydro-imidazo[1,2-c] pyrido[3,4-e] pyrimidin-5(6H)-one (Compound12).

(f) 2-(3-Chlorophenyl)-7,8,9,10-tetrahydro-imidazo[1,2-c] pyrido[3,4-e] pyrimidin-5(6H)-one (Compound 57), m.p. 320°–322° C.

EXAMPLE VII

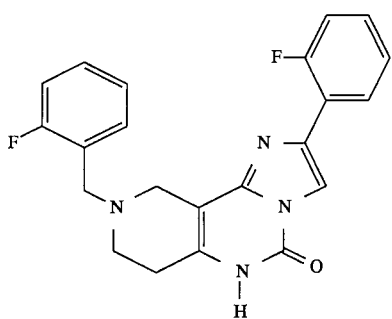

2-Fluorobenzyl bromide (54 μL, 0.45 mmol) was added to a solution of 2-(2-fluorophenyl)-7,8,9,10-tetrahydro-imidazo[1,2-c]pyrido[3,4-e] pyrimidin-5(6H)-one (128 mg, 0.45 mmol) and triethylamine (76 μL, 0.54 mmol) in DMF (1 mL) at room temperature. The reaction mixture was stirred for 45 minutes, and then concentrated. Aqueous sodium bicarbonate was added, the aqueous layer extracted twice with 10% methanol/ethyl acetate, and the combined organic layers dried over magnesium sulfate, filtered, concentrated, and triturated with methanol/ether to give 9-(2-Fluorobenzyl)-2-(2-fluorophenyl)-7,8,9,10-tetrahydro-imidazo[ 1,2-c]pyrido[3,4-e] pyrimidin-5(6H)-one (Compound 13) as an off-white solid, m.p. 270°–273° C. Treatment with ethanolic HCI affords the corresponding HCI salt.

EXAMPLE VIII

The following compounds were prepared according to the procedure described in Example VII:

(a) 9-Benzyl-2-(3-chlorophenyl)-7,8,9,10-tetrahydro-imidazo[ 1,2-c]pyrido[3,4-e] pyrimidin-5(5H)-one (Compound 14), as an off-white solid, m.p. 255°–256° C.

(b) 9-Benzyl-2-(3-fluorophenyl)-7,8,9,10-tetrahydro-imidazo[ 1,2-c]pyrido[3,4-e] pyrimidin-5(6H)-one (Compound 15), as a pale yellow solid, m.p. 273°–274° C.

(c) 9-Benzyl-2-(4-fluorophenyl)-7,8,9,10-tetrahydro-imidazo[ 1,2-c]pyrido[3,4-e] pyrimidin-5(6H)-one (Compound 16), as an off white solid, m.p. 272°–274° C.

(d) 9-Benzyl-2-(4-methoxyphenyl)-7,8,9,10-tetrahydro-imidazo[ 1,2-c]pyrido[3,4-e] pyrimidin-5(6H)-one (Compound 17).

(e) 9-Benzyl-2-(2-fluorophenyl)-7,8,9,10-tetrahydroimidazo[ 1,2-c]pyrido[3,4-e] pyrimidin-5(6H)-one (Compound 18), as an off white solid, m.p. 281°–282° C.

(f) 9-Benzyl-2-phenyl-7,8,9,10-tetrahydro-imidazo[1,2-c] pyrido[3,4-e] pyrimidin-5(6H)-one (Compound 19).

(g) 9-(2-pyrimidinyl)-2-(2-fiuorophenyl)-7,8,9,10-tetrahydroimidazo[ 1,2-c]pyrido[3,4-e] pyrimidin-5(6H)-one (Compound 20), as an off white solid, m.p. >270° C.

(h) ±9-(α-Methylbenzyl)-2-(2-fiuorophenyl)-7,8,9,10-tetrahydro-imidazo[ 1,2-c]pyrido[3,4-e] pyrimidin-5(6H)-one (Compound 21), as an off white solid, m.p. 265°–266° C.

(i) 9-(4-Fluorobenzyl)-2-(2-fluorophenyl)-7,8,9,10-tetrahydro-imidazo[ 1,2-c]pyrido{3,4-e]pyrimidin-5(6H)-one (Compound 22), as an off white solid, m.p. >270° C.

(j) 9-(4-Methoxybenzyl)-2-(2-fiuorophenyl)-7,8,9,10-tetrahydro-imidazo[ 1,2-c]pyrido[3,4-e] pyrimidin-5(6H)-one (Compound 23), as a tan solid, m.p. >270° C.

(k) 9-(4-Methylbenzyl)-2-(2-fiuorophenyl)-7,8,9,10-tetrahydro-imidazo[ 1,2-c]pyrido{3,4-e]pyrimidin-5(6H)-one (Compound 24), as an off white solid, m.p.255°–267° C.

(l) 9-(3,4-Difluorobenzyl)-2-(2-fluorophenyl)-7,8,9,10-tetrahydro-imidazo[ 1,2-c]pyrido[3,4-e]pyrimidin-5(6H)-one (Compound 25), as an off white solid, m.p. 271°–273° C.

(m) 9-(2,4-Difluorobenzyl)-2-(2-fluorophenyl)-7,8,9,10-tetrahydro-imidazo[ 1,2-c]pyrido[3,4-e]pyrimidin-5(6H)-one (Compound 26), as an off white solid, m.p. 270°–272° C.

(n) ±9-(4-Fluoro-α-Methylbenzyl)-2-(2-fluorophenyl)-7,8,9,10-tetrahydro-imidazo[1,2-c]pyrido[3,4-e]pyrimidin-5(6H)-one mono hydrochloride (Compound 27), as an off white solid, m.p. 278°– 280° C.

(o) 9-(3-Fluorobenzyl)-2-(2-fluorophenyl)-7,8,9,10-tetrahydro-imidazo[ 1,2-c]pyrido[3,4-e] pyrimidin-5(6H)-one (Compound 28), as an off white solid, m.p. 268°–269° C.

(p) ±9-(3-Fluoro-α-methylbenzyl)-2-(2-fluorophenyl)-7,8,9,10-tetrahydro-imidazo[1,2-c]pyrido[3,4-e]pyrimidin-5(6H)-one (Compound 29), as an off white solid, m.p.262°–264° C.

(q) 9-(2-methylbenzyl)-2-(2-fluotophenyl)-7,8,9,10-tetrahydro-imidazo[ 1,2-c]pyrido[3,4-e]pyrimidin-5(6H)-one (Compound 30), as a white solid, m.p. 287°–289° C.

(r) ±9-(2-Fluoro-α-methylbenzyl)-2-(2-fluorophenyl)-7,8,9,10-tetrahydro-imidazo[1,2-c]pyrido[3,4-e]pyrimidin-5(6H)-one (Compound 31), as an off white solid, m.p. 272°–274° C.

(s) ±9-(1-indanyl)-2-(2-fluorophenyl)-7,8,9,10-tetrahydro-imidazo[ 1,2-c]pyrido[3,4-e]pyrimidin-5(6H)-one (Compound 32).

(t) 9-(2-propyl)-2-(2-fluorophenyl)-7,8,9,10-tetrahydro-imidazo[ 1,2-c]pyrido[3,4-e]pyrimidin-5(6H)-one (Compound 33).

(u) 9-cyclohexylmethyl-2-(2-fluorophenyl)-7,8,9,10-tetrahydro-imidazo[ 1,2-c]pyrido[3,4-e]pyrimidin-5(6H)-one (Compound 34), as a white solid, m.p.265°–267° C.

(v) ±9-benzyl-2-(2-fluorophenyl)-8-methyl-7,8,9,10-tetrahydro-imidazo[ 1,2-c]pyrido[3,4-e]pyrimidin-5(6H)-one (Compound 35).

EXAMPLE IX

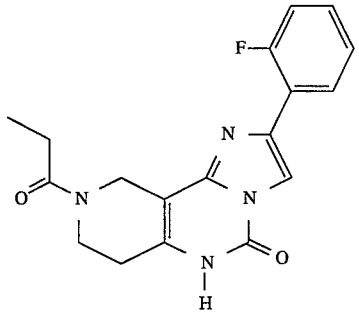

Propionyl chloride (39 μL, 0.4 mmol) was added to a solution of 2-( 2-fluorophenyl)-7,8,9,10-tetrahydro-imidazo[1,2-c]pyrido[3,4-e] pyrimidin-5-(6H)-one (124 mg, 0.4 mmol) and triethylamine (74 μL, 0.5 mmol) in DMF (2 mL) at room temperature. The reaction mixture was stirred for 50 minutes, and then poured into ice water. The precipitate was collected, washed with water and 95% ethanol, and dried to yield 9-propionyl- 2-(2-fluorophenyl)-7,8,9,10-tetrahydro-imidazo[1,2c-pyrido[ 3,4-e]pyrimidin-5(6H)-one (Compound 36) as a white solid, m.p. >310° C.

EXAMPLE X

The following compounds were prepared according to the procedure described in Example IX:

(a) 9-Butyryl-2-(2-fluorophenyl)-7,8,9,10-tetrahydroimidazo[ 1,2-c]pyrido[3,4-e]pyrimidin-5(6H)-one (Compound 37), as a white solid, m.p. 309°–311° C.

(b) 9-Hexanoyl-2-(2-fluorophenyl)-7,8,9,10-tetrahydroimidazo[ 1,2-c]pyrido[3,4-e]pyrimidin-5(6H)-one, (Compound 38), as a white solid, re.p. 295°–297° C.

(c) 9-Phenylacetyl-2-(2-fluorophenyl)-7,8,9,10-tetrahydro-imidazo[ 1,2-c]pyrido[3,4-e]pyrimidin-5(6H)-one (Compound 39), as an off-white solid, m.p. 307°–309° C.

(d) 9-Acetyl-2-(2-fluorophenyl)-7,8,9,10-tetrahydro-imidazo[ 1,2-c]pyrido[3,4-e] pyrimidin-5(6H)-one (Compound 40), as an off-white solid, m.p. >315° C.

(e) 9-Nicotinoyl-2-(2-fluorophenyl)-7,8,9,10-tetrahydroimidazo[ 1,2-c]pyrido[3,4-e]pyrimidin-5(6H)-one (Compound 41), as an off-white solid, m.p, 280°–282° C.

(f) 9-Isonicotinoyl-2-(2-fluorophenyl)-7,8,9,10-tetrahydroimidazo[ 1,2-c]pyrido[3,4-e] pyrimidin-5(6H)-one (Compound 42), as an off-white solid, m.p. >300° C.

(g) 9-Picolinoyl-2-(2-fluorophenyl)-7,8,9,10-tetrahydroimidazo[ 1,2-c]pyrido[3,4-e] pyrimidin-5(6H)-one (Compound 43), as an off-white solid, m.p. 287°–290° C.

EXAMPLE XI

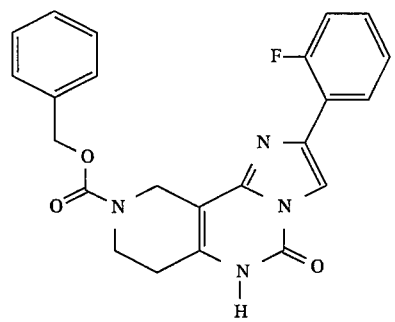

Benzyl chloroformate (57 μL, 0.4 mmol) was added to a solution of 2-(2-fluorophenyl)-7,8,9, 10-tetrahydro-imidazo[ 1,2-c]pyrido[3,4-c] pyrimidin-5(6H)-one (124 mg, 0.4 mmol) and triethylamine (74 μL, 0.5 mmol) in DMF (1 mL) at room temperature. The reaction mixture was stirred for 1 hour, then poured into ice water. The precipitate was collected, washed with 95% ethanol and ether, and subsequently dried to give 9-Carbobenzyloxy-2-(2-fiuorophenyl)-7,8,9,10-tetrahydro-imidazo [1,2-c]pyrido[3,4-e]pyrimidin-5(6H)-onc (Compound 44). Recrystallization from aqueous ethanol afforded Compound 41 as an off-white solid, m.p. 250° C. (d).

EXAMPLE XII

The following compounds were prepared according to the procedure described in Example XI:

(a) 9-Carboethoxy-2-(2-fluorophenyl)-7,8,9,10-tetrahydro-imidazo[ 1,2-c]pyrido[3,4-e]pyrimidin-5(6H)-one (Compound 45) as a white solid, m.p. 297°–299° C. (d).

(b) 9-Carbobutoxy-2-(2-fluorophenyl)-7,8,9,10-tetrahydro-imidazo[ 1,2-c]pyrido[3,4-e]pyrimidin-5(6H)-one (Compound 46) as a white solid, m.p. 268°–269° C.

(c) 9-Phenylsulfonyl-2-(2-fluorophenyl)-7,8,9,10-tetrahydroimidazo[ 1,2-c]pyrido[3,4-e]pyrimidin-5(6H)-one (Compound 47).

EXAMPLE XIII

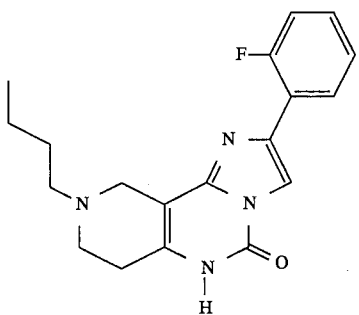

To 2-(2-fluorophenyl)-7,8,9,10-tetrahydro-imidazo[1,2-c]pyrido [3,4-e]pyrimidin-5(6H)-one(171 mg, 0.6 mmol) in pH4–5 HCL-methanol (6 mL) at room temperature was added n-butyraldehyde (53 μL, 0.6 mmol) and sodium cyanoborohydride (38 mg, 0.6 mmol). After the reaction mixture was stirred for 6 hours, concentrated HCl was added until the mixture became homogenous. The mixture was then diluted with water (5 mL) and extracted twice with ether. The aqueous layer was made alkaline with aqueous ammonium hydroxide, saturated with sodium chloride, and extracted twice with 10% methanol/ethyl acetate. The combined organic layers were dried over magnesium sulfate, filtered and concentrated to give 9-n-Butyl-2-(2-fluorophenyl)-7,8,9,10-tetrahydro-imidazo[ 1,2-c]pyrido[3,4-e]pyrimidin-5(6H)-one (Compound 48). Recrystallization from aqueous ethanol gave a white fluffy solid, m.p. 251°–253° C. (d).

EXAMPLE XIV

The following compounds were prepared according to the procedure described in Example XIII:

(a) 9-Methyl-2-(2-fluorophenyl)-7,8,9,10-tetrahydro-imidazo[ 1,2-c]pyrido[3,4-e] pyrimidin-5(6H)-one (Compound 49) as a yellow solid, m.p. 290°–291° C.

(b) 9-(2-Phenylethyl)-2-(2-fluorophenyl)-7,8,9,10-tetrahydro-imidazo[ 1,2-c]pyrido[3,4-e]pyrimidin-5(6H)-one (Compound 50) as a cream-colored solid, m.p. 264°–266° C.

(c) 9-(3-Phenylpropyl)-2-(2-fluorophenyl)-7,8,9,10-tetrahydro-imidazo[ 1,2-c]pyrido[3,4-e]pyrimidin-5(6H)-one (Compound 51) as a white fluffy solid, m.p. 244°–245° C.

EXAMPLE XV

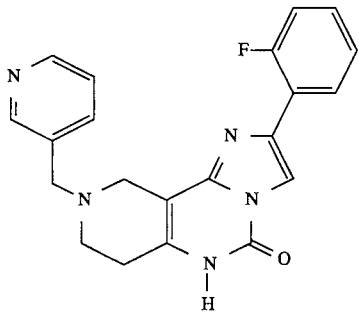

A mixture of 9-(Nicotinoyl)-2-(2-fluorophenyl)-7,8,9,10-tetrahydro-imidazo[ 1,2-c]pyrido[3,4-e] pyrimidin-5(6H)-one (128 mg. 0.33 mmol), methylene chloride (3 mL) and 1M borane in THF (3.3 mL) was stirred at room temperature for 16 h. The reaction mixture was carefully acidified with 5 mL of 6N HCl and heated at reflux for 15 min. The reaction mixture was made alkaline with 10% NaOH and the product was extracted with 10% methanol in ethyl acetate. After drying over magnesium sulfate the solvent was removed in vacuo to afford a yellow solid which was recrystallized from ethanol to afford 9-(3-Pyridylmethyl)-2-fluorophenyl)-7,8,9,10-tetrahydro-imidazo[1,2-c] pyrido [3,4-e] pyrimidin-5(6H)-one (Compound 52) as a pale yellow solid, m.p. 290°–292° C.

EXAMPLE XVI

The following compounds were prepared according to the procedure described in Example XV:

(a) 9-(2-Pyridylmethyl)-2-fluorophenyl)-7,8,9,10-tetrahydro-imidazo[ 1,2-c]pyrido[3,4-e] pyrimidin-5(6H)-one (Compound 53).

(b) 9-(4-Pyridylmethyl)-2-fluorophenyl)-7,8,9,10-tetrahydro-imidazo[ 1,2-c]pyrido[3,4-e] pyrimidin-5(6H)-one (Compound 54), as an off white solid, m.p. 293°–294° C.

EXAMPLE XVII

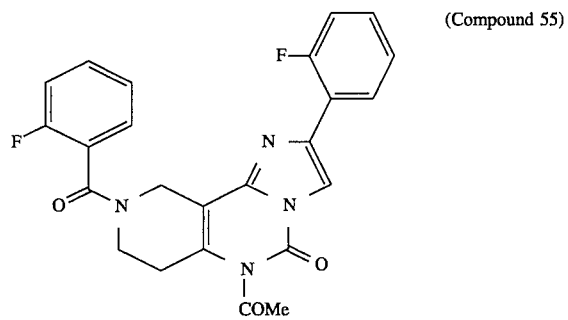
(Compound 55)

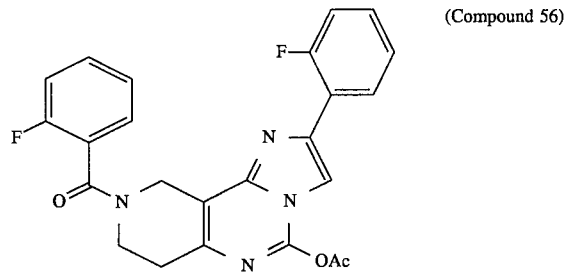
(Compound 56)

A mixture of 9-(2-fluorobenzyl)-2-(2-fluorophenyl)-7,8, 9,10-tetrahydro-imidazo[ 1,2-c]pyrido[3,4-e] pyrimidin-5(6H)-one (392 mg, 1 mmol) and 50% sodium hydride(144 mg, 3 mmol) in DMF (5 mL) was stirred at room temperature for 15 min. Acetyl chloride (1 mL) was added and stirring was continued for 30 min. The reaction was diluted with ethyl acetate and washed with water. After drying over magnesium sulfate, the solvent was removed in vacuo and the residue was subjected to flash chromatography on silica gel with 30% ethyl acetate in hexane as the eluent to afford 6-acetyl-9-(2-fluorobenzyl)- 2-(2-fluorophenyl)-7,8,9,10-tetrahydro-imidazo[l,2-c]pyrido[3,4-e] pyrimidin-5(6H)-one (compound 55) and 5-acetoxy-9-(2-fluorobenzyl)- 2-(2-fluorophenyl)-7,8,9,10-tetrahydro-imidazo[1,2c]pyrido[3, 4-e] pyrimidine (compound 56) as white solids.

EXAMPLE XVIII

The following additional examples were prepared according to the procedure described in Example VII:

(a) 9-Benzyl-2-(4-chlorophenyl)-7,8,9,10-tetrahydro-imidazo[ 1,2-c]pyrido[3,4-e] pyrimidin-5(6H)-one (Compound 58).

(b) 9-Ethyl-2-(2-fluorophenyl)-7,8,9,10-tetrahydro-imidazo[ 1,2-c]pyrido[3,4-e] pyrimidin-5(6H)-one (Compound 59), as an off-white solid, m.p. 266°–268° C.

(c) 9-Allyl-2-(2-fluorophenyl)-7,8,9,10-tetrahydro-imidazo[ 1,2-c]pyrido[3,4-e] pyrimidin-5(6H)-one (Compound 60), as an off-white solid, m.p. 270°–273° C.

(d) 9-Cyclpropylmethyl-2-(2-fluorophenyl)-7,8,9,10-tetrahydro-imidazo[ 1,2-c]pyrido[3,4-e] pyrimidin-5(6H)-one (Compound 61), as an off-white solid, m.p.>275° C.

(e) 9-(4(5)-Imidazoylmethyl)-2-(2-fluorophenyl)-7,8,9, 10-tetrahydro-imidazo[ 1,2-c]pyrido[3,4-e] pyrimidin-5(6H)-one (Compound 62), as an off-white solid, m.p. 275°–277° C.

(f) 9-Benzyl-2-(2,4-difluorophenyl)-7,8,9,10-tetrahydro-imidazo[ 1,2-c]pyrido[3,4-e] pyrimidin-5(6H)-one (Compound 63), as an off-white solid, m.p. 275°–277° C.

(g) 9-Benzyl-2-(2-fluoro-4-methoxyphenyl)-7,8,9,10-tetrahydro-imidazo[ 1,2-c]pyrido[3,4-e] pyrimidin-5(6H)-one (Compound 64), as an off-white solid, m.p. 257°–261° C.

(h) 9-(2-Thienylmethyl)-2-(fluorophenyl)-7,8,9,10-tetrahydro-imidazo[ 1,2-c]pyrido[3,4-e] pyrimidin-5(6H)-one (Compound 65), as an off-white solid, m.p. 270°–271° C.

(i) 9-(2-Imidazoylmethyl)-2-(2-fluorophenyl)-7,8,9,10-tetrahydro-imidazo[ 1.2-c]pyrido[3,4-e] pyrimidin-5(6H)-one (Compound 66), as an off-white solid, m.p. 210°–215° C.

(k) 9-Methyl-2-(4-methoxyphenyl)-7,8,9,10-tetrahydro-imidazo[ 1,2-c]pyrido[3,4-e] pyrimidin-5(6H)-one (Compound 67), as an off-white solid, m.p. 264°–267° C.

(l) 9-Benzyl-2-(4-methylphenyl)-7,8,9,10-tetrahydro-imidazo[ 1,2-c]pyrido[3,4-e] pyrimidin-5(6H)-one (Compound 68), as an off-white solid, m.p. 255°–258° C.

(m) 9-Methyl-2-(2-fluoro-4-methoxyphenyl)-7,8,9,10-tetrahydro-imidazo[ 1,2-c]pyrido[3,4-e] pyrimidin-5(6H)-one (Compound 69).

(n) 9-Benzyl-2-(3,4-difluorophenyl)-7,8,9,10-tetrahydro-imidazo[ 1,2-c]pyrido[3,4-e] pyrimidin-5(6H)-one (Compound 70), as an off-white solid, m.p. 268°–271° C.

(o) 9-Benzyl-2-(3-methoxyphenyl)-7,8,9,10-tetrahydro-imidazo[ 1,2-c]pyrido[3,4-e] pyrimidin-5(6H)-one (Compound 71), as an off-white solid, m.p. 269°–271° C.

(p) 9-Benzyl-2-(2-thienyl)-7,8,9,10-tetrahydro-imidazo [1,2-c]pyrido[ 3,4-e] pyrimidin-5(6H)-one (Compound 72), as an off-white solid, m.p. 271°–274° C.

(q) 9-Benzyl-2-(2-methoxyphenyl)-7,8,9,10-tetrahydro-imidazo[ 1,2-c]pyrido[3,4-e] pyrimidin-5(6H)-one (Compound 73).

(r) 9-Benzyl-2-(2,5-difluorophenyl)-7,8,9,10-tetrahydro-imidazo[ 1,2-c]pyrido[3,4-e] pyrimidin-5(6H)-one (Compound 74).

What is claimed is:

1. A compound of the formula:

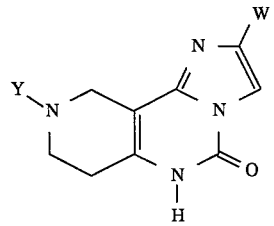

or the pharmaceutically acceptable non-toxic salts thereof wherein

W is phenyl, 2- or 3-thienyl or 2-, 3-, or 4-pyridyl; or phenyl, 2- or 3-thienyl or 2-, 3-, or 4-pyridyl, each of which is mono or disubstituted with halogen, lower alkyl, or straight or branched chain lower alkoxy having 1–6 carbon atoms; and Y is
i) hydrogen, phenyl, 2- or 3-thienyl, 2-, 3- or 4-pyridyl, 2- or 4(5)-imidazolyl, 2-pyrimidinyl, or 1-indanyl;
ii) phenyl, 2- or 3-thienyl, 2-, 3- or 4-pyridyl, 2- or 4(5)-imidazolyl, or 2-pyrimidinyl, each of which is mono or disubstituted with halogen, lower alkyl having 1–6 carbon atoms, lower alkoxy having 1–6 carbon atoms, or alkoxylalkyl where the alkoxy portion is straight or branched chain alkoxy having 1–6 carbon atoms and the alkyl portion is straight or branched chain alkyl having 1–6 carbon atoms;
iii) straight or branched chain alkyl having 1–6 carbon atoms;
iv) straight or branched chain alkyl having 1–6 carbon atoms, wherein each alkyl is substituted with the groups of ii;
v) cycloalkyl having 3–10 carbon atoms, cycloalkyl alkyl where the cycloalkyl portion has 3–7 carbon atoms and the alkyl portion has 1–6 carbon atoms;
vi) aminoalkyl where the alkyl portion is straight or branched chain alkyl having 1–6 carbon atoms, or mono or dialkyl aminoalkyl where each alkyl is a straight or branched chain alkyl having 1–6 carbon atoms; or
vii) $COR_7$ or $SO_2R_7$ where $R_7$ is straight or branched chain lower alkyl having 1–6 carbon atoms, phenyl, 2- or 3-thienyl, 2-, 3- or 4-pyridyl, 2- or 4(5)-imidazolyl, or 2-pyrimidinyl; or $R_7$ is phenyl, 2- or 3-thienyl, 2-, 3- or 4-pyridyl, 2- or 4(5)-imidazolyl, or 2-pyrimidinyl each of which may be mono or disubstituted with halogen, lower alkyl having 1– 6 carbon atoms, straight or branched alkoxy having 1–6 carbon atoms, or alkoxyalkyl where the alkoxy portion is straight or branched chain alkoxy having 1–6 carbon atoms and the alkyl portion is straight or branched chain alkyl having 1–6 carbon atoms.

2. A compound according to claim 1, wherein W is phenyl monosubstituted with chlorine or fluorine.

3. A compound according to claim 1, wherein W is phenyl monosubstituted with fluorine.

4. A compound according to claim 1, wherein Y is 3-phenylpropyl.

5. A compound according to claim 1, wherein Y is acetyl.

6. A compound according to claim 1, wherein Y is carboethoxy.

7. A compound according to claim 1, wherein Y is butyl.

8. A compound according to claim 1, wherein Y is benzyl.

9. A compound according to claim 1, wherein Y is hexanoyl.

10. A compound according to claim 1, wherein Y is methyl.

11. A compound according to claim 1, wherein Y is carbobenzyloxy.

12. A compound according to claim 1, wherein Y is hydrogen.

* * * * *